(12) United States Patent
Kadykowski

(10) Patent No.: US 7,547,314 B2
(45) Date of Patent: Jun. 16, 2009

(54) SELF-CLEANING ENDOSCOPIC VEIN HARVESTER ROD

(75) Inventor: Randal James Kadykowski, South Lyon, MI (US)

(73) Assignee: TERUMO Cardiovascular Systems Corporation, Ann Arbor, MI (US)

( * ) Notice: Subject to any disclaimer, the term of this patent is extended or adjusted under 35 U.S.C. 154(b) by 488 days.

(21) Appl. No.: 11/441,589

(22) Filed: May 26, 2006

(65) Prior Publication Data

US 2007/0276418 A1 Nov. 29, 2007

(51) Int. Cl.
*A61D 1/02* (2006.01)
(52) U.S. Cl. ....................................... 606/159
(58) Field of Classification Search .................. 606/39, 606/40, 159, 167, 168, 170; 604/22; 30/41, 30/41.5, 114, 123, 123.3, 128, 280, 289; 83/168
See application file for complete search history.

(56) References Cited

U.S. PATENT DOCUMENTS

| | | | |
|---|---|---|---|
| 4,793,346 A | 12/1988 | Mindich | |
| 5,814,059 A | 9/1998 | Hart et al. | |
| 5,817,013 A | 10/1998 | Ginn et al. | |
| 5,928,138 A | 7/1999 | Knight et al. | |
| 6,022,313 A | 2/2000 | Ginn et al. | |
| 6,036,713 A | 3/2000 | Kieturakis | |
| 6,042,558 A | 3/2000 | Hoyne et al. | |
| 6,077,289 A | 6/2000 | Mollenauer | |
| 6,592,604 B2 | 7/2003 | Hess et al. | |
| 6,660,016 B2 | 12/2003 | Lindsay | |
| 6,740,102 B2 | 5/2004 | Hess et al. | |
| 6,887,251 B1 | 5/2005 | Suval | |
| 6,951,568 B1 | 10/2005 | Chin | |
| 2003/0130674 A1 | 7/2003 | Kasahara et al. | |
| 2004/0162462 A1 | 8/2004 | Knighton et al. | |
| 2004/0204719 A1 | 10/2004 | Fogarty et al. | |
| 2004/0230215 A1* | 11/2004 | Eriksson et al. | 606/180 |
| 2005/0004586 A1 | 1/2005 | Suval | |
| 2005/0010242 A1 | 1/2005 | Lindsay | |
| 2005/0154415 A1 | 7/2005 | Fogarty et al. | |
| 2005/0159764 A1* | 7/2005 | Kasahara et al. | 606/159 |

* cited by examiner

*Primary Examiner*—Todd E Manahan
*Assistant Examiner*—Kevin Everage
(74) *Attorney, Agent, or Firm*—Mark Mollan, Esq.; Gael Diane Tisack, Esq.; MacMillan, Sobanski, & Todd, LLC

(57) ABSTRACT

An endoscopic vessel harvesting device has an elongated sleeve member for insertion into a body having a vessel to be harvested. A V-cutter cutter is provided that is longitudinally extendable from the sleeve member toward a cutting position for cutting branches of a vessel being harvested. The cutter comprises a V-tip, a longitudinal slit for receiving a branch to be cut, and electrodes adjacent to the longitudinal slit for being electrically energized to cut and cauterize the branch. A debris remover is fixed to the sleeve member in alignment with the longitudinal slit for mechanically removing debris from the longitudinal slit when the cutter is positioned longitudinally inward from the cutting position. The debris remover is operable during times that the sleeve member is inserted into the body. Effectiveness of the V-cutter is maintained even in conditions favoring a build-up of debris that could otherwise clog the longitudinal slit of the V-cutter.

6 Claims, 5 Drawing Sheets

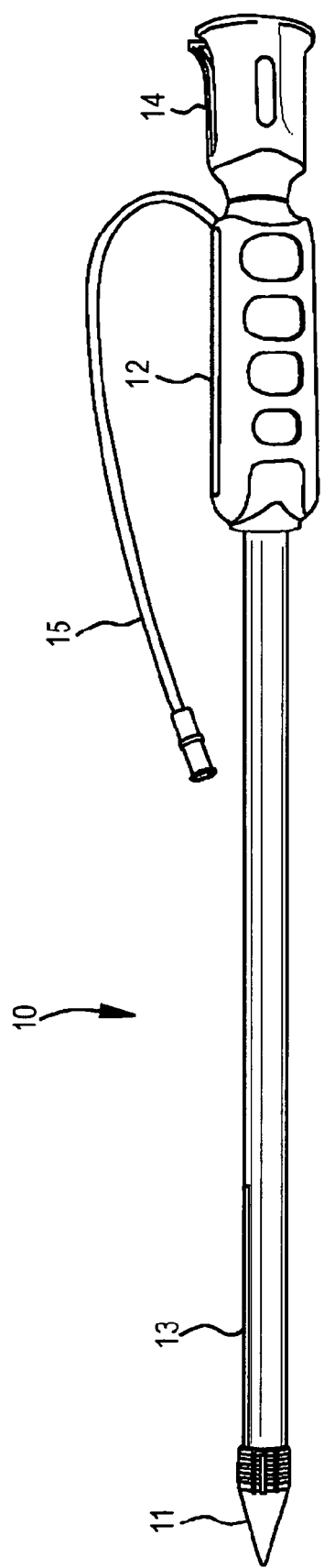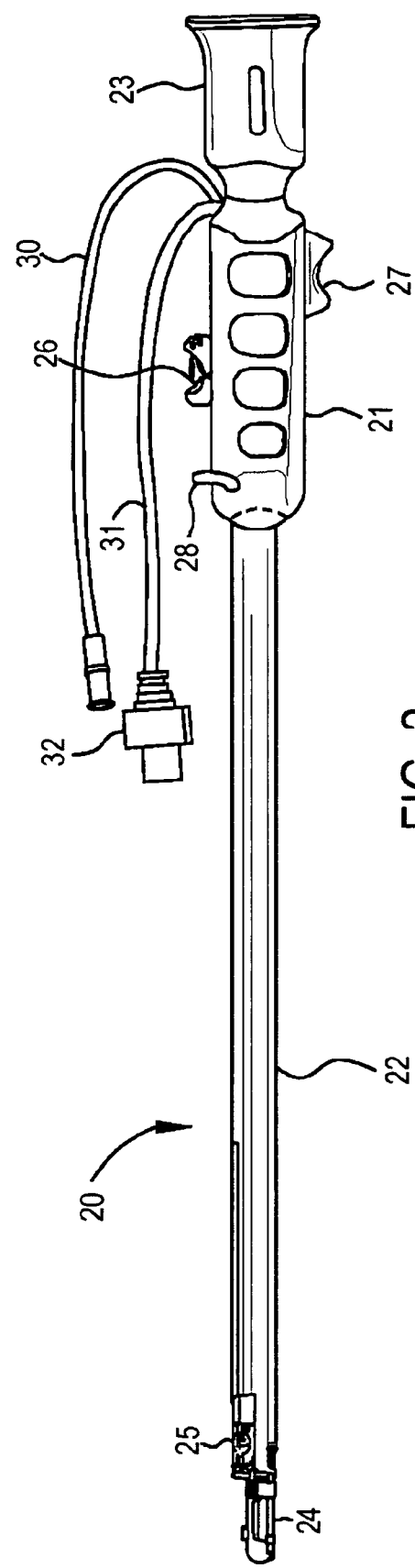

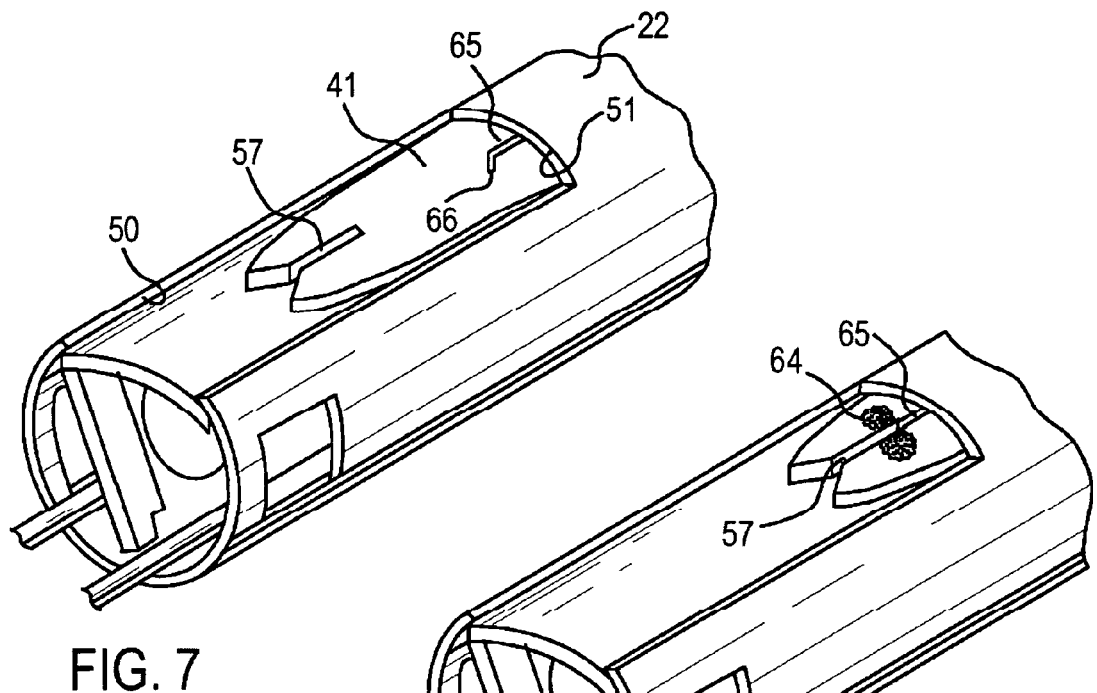
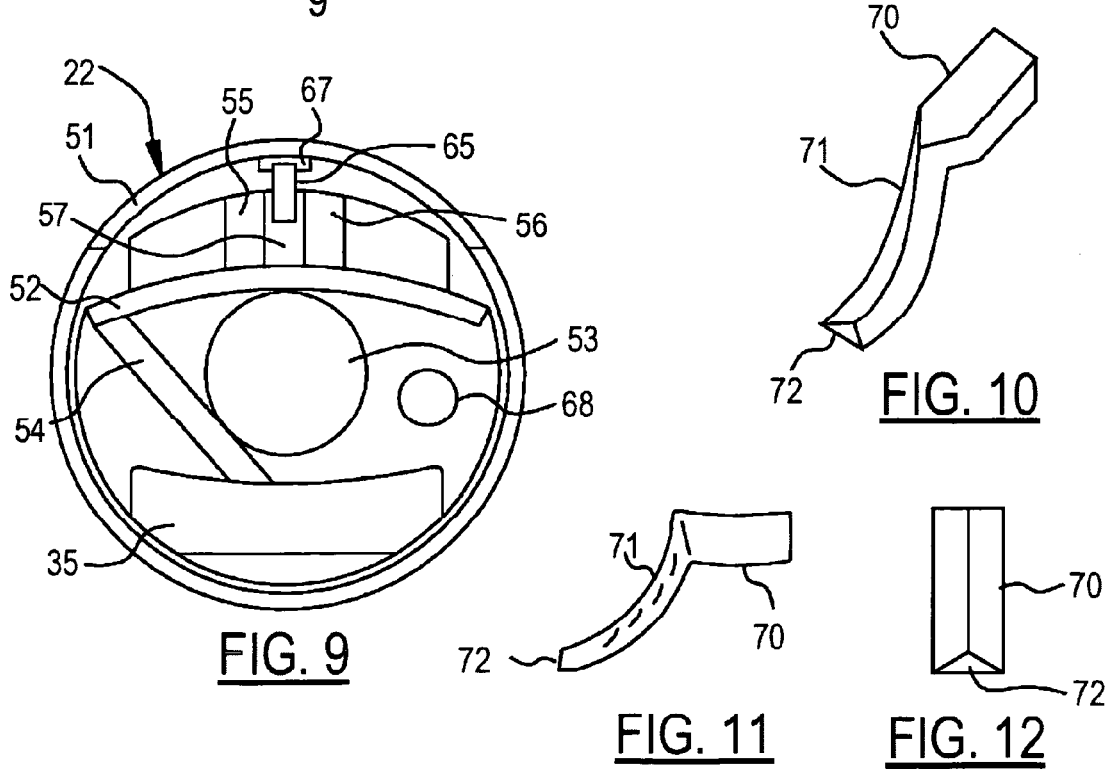

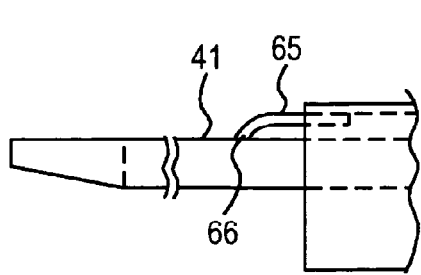
FIG. 13
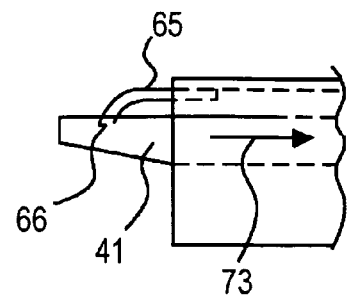
FIG. 14
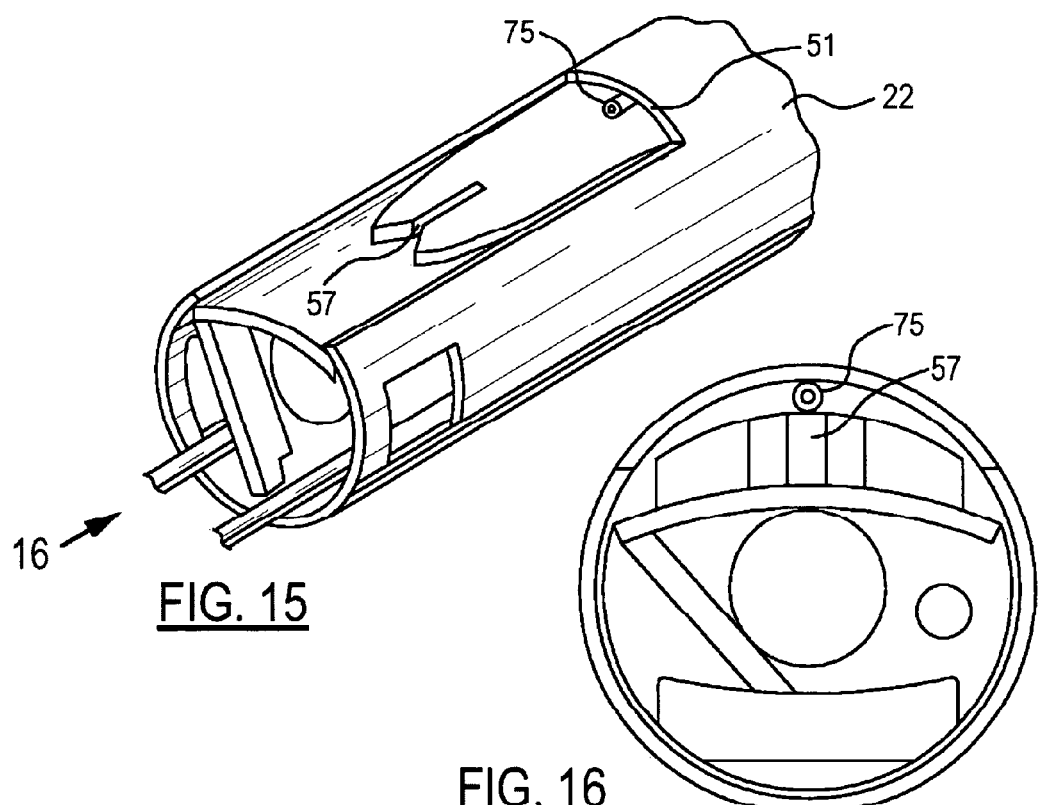
FIG. 15
FIG. 16
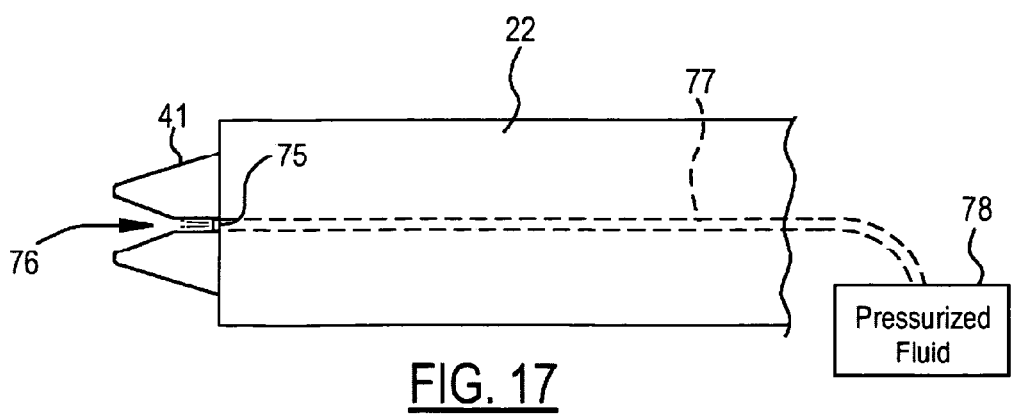
FIG. 17

SELF-CLEANING ENDOSCOPIC VEIN HARVESTER ROD

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to endoscopic harvesting of blood vessels, and, more specifically, to avoiding buildup of debris on a endoscopic cutting tool used to severe branches from a blood vessel being harvested.

The present invention relates to the harvesting of blood vessels and, more particularly, to methods and apparatus for endoscopic dissection and retraction of sections of blood vessels, such as saphenous veins, for use as a coronary artery bypass graft.

In connection with coronary artery bypass grafting (CABG), a blood vessel or vessel section, such as an artery or vein, is "harvested" (i.e., removed) from its natural location in a patient's body and to use it elsewhere in the body. In CABG surgery, the blood vessel is used to form a bypass between an arterial blood source and the coronary artery that is to be bypassed. Among the preferred sources for the vessel to be used as the bypass graft are the saphenous veins in the legs and the radial artery in the arms.

Endoscopic surgical procedures for harvesting a section of a vein (e.g., the saphenous vein) subcutaneously have been developed in order to avoid disadvantages and potential complications of harvesting through a continuous incision (e.g., along the leg) for the full length of the desired vein section in order to provide adequate exposure for visualizing the vein and for introducing surgical instruments to sever, cauterize and ligate the tissue and side branches of the vein. One such minimally-invasive technique employs a small incision for locating the desired vein and for introducing one or more endoscopic harvesting devices. Primary dissection occurs by introduction of a dissecting instrument through the incision to create a working space and separate the vein from the surrounding tissue. Then a cutting instrument is introduced into the working space to severe the blood vessel from the connective tissue surrounding the section to be harvested and any side branches of the blood vessel. The branches may be clipped and/or cauterized.

In one typical procedure, the endoscopic entry site is located near the midpoint of the vessel being harvested, with dissection and cutting of branches proceeding in both directions along the vessel from the entry site. In order to remove the desired section of the blood vessel, a second small incision, or stab wound, is made at one end thereof and the blood vessel section is ligated. A third small incision is made at the other end of the blood vessel section which is then ligated, thereby allowing the desired section to be completely removed through the first incision. Alternatively, only the first two incisions may be necessary if the length of the endoscopic device is sufficient to obtain the desired length of the blood vessel while working in only one direction along the vessel from the entry point.

An example of a commercially available product for performing the endoscopic vein harvesting described above is the VirtuoSaph™ Endoscopic Vein Harvesting System from Terumo Cardiovascular Systems Corporation of Ann Arbor, Mich. Endoscopic vein harvesting systems are also shown in U.S. Pat. No. 6,660,016 to Lindsay and U.S. patent application publication 2005/0159764A1 in the name of Kasahara et al, both of which are incorporated herein by reference in their entirety.

In the VirtuoSaph™ System and Kasahara et al, the cutting tool for severing and cauterizing branches has the form of a V-cutter wherein a V-shaped tip at the distal end of the cutter guides a branch to be cut into a longitudinal slit. Electrodes adjacent the slit are electrically energized with a high frequency voltage in order to sever and cauterize the branch by extreme heating. During the process of cutting and cauterizing the many branches coming from the vein being harvested, fat, connective tissue, burnt residue, and other body material builds-up on the V-cutter thereby reducing the effectiveness of the cutting operation. The amount of debris build-up depends in part on the physiology of the patient. With excessive build-up, known systems have required medical personnel to remove the harvesting rod from the patient in order to clear away this debris so that effective cutting can be resumed. Such removal undesirably complicates the procedure and prolongs it. Thus, it would be desirable to reduce patient risks by avoiding the need to remove the harvesting rod in order to clear debris from the area of the longitudinal slit in the V-cutter.

SUMMARY OF THE INVENTION

The present invention has the advantage of maintaining effectiveness of a V-cutter even in conditions favoring a build-up of debris that could otherwise clog the longitudinal slit of the V-cutter.

In one aspect of the invention, an endoscopic vessel harvesting device is provided having an elongated sleeve member for insertion into a body having a vessel to be harvested. A cutter is provided that is longitudinally extendable from the sleeve member toward a cutting position for cutting branches of a vessel being harvested. The cutter comprises a V-tip, a longitudinal slit for receiving a branch to be cut, and electrodes adjacent to the longitudinal slit for being electrically energized to cut and cauterize the branch. A debris remover is fixed to the sleeve member in alignment with the longitudinal slit for mechanically removing debris from the longitudinal slit when the cutter is positioned longitudinally inward from the cutting position. The debris remover is operable during times that the sleeve member is inserted into the body.

BRIEF DESCRIPTION OF THE DRAWINGS

FIG. 1 is a side view of a disposable dissector rod of the invention.

FIG. 2 is a side view of a disposable harvester rod of the invention.

FIG. 7 is a perspective view of the harvester rod showing a wiper arm of the invention with the V-cutter partially extended.

FIG. 8 is a perspective view of the harvester rod with the V-cutter fully retracted so that the wiper arm of FIG. 7 clears debris from the slit.

FIG. 9 is an end view of the harvester rod of FIG. 8.

FIGS. 10-12 show one preferred profile of the wiper arm of FIG. 7.

FIGS. 13 and 14 are side views of the action of the wiper arm against the V-cutter in extended and retracted positions, respectively.

FIG. 15 is a perspective view of an alternative embodiment of the harvester rod having a fluid nozzle for clearing debris.

FIG. 16 is an end view of the harvester rod of FIG. 15.

FIG. 17 is a top view of the fluid nozzle with the V-cutter in a retracted position.

DETAILED DESCRIPTION OF PREFERRED EMBODIMENTS

Figure 3:
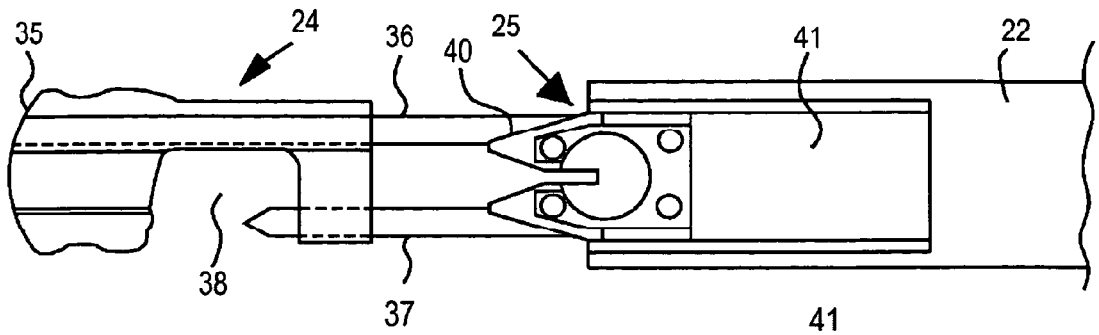
FIG. 3 is a top view of the distal end of the harvester rod.

Referring to FIG. 1, a disposable dissector rod 10 is shown of the type for endoscopic dissection of a saphenous vein or other vessel by insertion through an initial incision and then pressing a dissector tip 11 into the fat along the direction of the vessel to separate it from adjacent tissue. Dissector rod 10 has a handle 12 connected to an elongated sleeve 13 having dissector tip 11 at its distal end. A receiver 14 at the end of handle 12 receives an endoscope (not shown) for extending through sleeve 13 to dissector tip 11 which is transparent in order to allow visualization of the vessel and surrounding tissue. An insufflation tube 15 may be connected to a source of $CO_2$ gas for filling the cavity adjacent the vessel as it is being formed in a conventional manner.

After initial blunt dissection around the vein, a harvester rod 20 as shown in FIG. 2 is used to grasp the vessel being dissected and to sever any branches or connective tissue connecting to the vessel. Harvester rod 20 has a handle 21 connected to an elongated sleeve member 22 and an endoscope receiver 23. At the distal end of sleeve 22 are a V-keeper 24 for retaining the vessel being dissected and a V-cutter 25 for severing branches. V-keeper 24 is manipulated by V-keeper buttons 26 on handle 21. V-cutter 25 is extended or retracted by manipulating a V-cutter extender button 27 on handle 21. An endoscope wiper lever 28 is provided on handle 21 for controlling a wiper that clears the end of the endoscope when the endoscope optics become covered by material in the body cavity. An insufflator tube 30 can be connected to a source of gas such as $CO_2$ to deliver the gas to the distal end of sleeve 22. A bipolar cord 31 has a connector 32 at one end for connecting to a source of high frequency voltage, and includes conductors for supplying the voltage to electrodes on V-cutter 25 as explained below.

V-keeper 24 and V-cutter 25 are shown in greater detail in FIG. 3. V-keeper 24 includes a guide 35 mounted to a support rod 36 and a movable rod 37. The vein or other vessel to be harvested is maneuvered into an opening 38 and then the V-keeper buttons on the handle are manipulated to extend rod 37 to close the opening and thereby retain the vessel. V-cutter 25 includes a V-tip 40 mounted to an extendable guide 41 that is manipulated by the V-cutter button on the handle.

Figure 4:
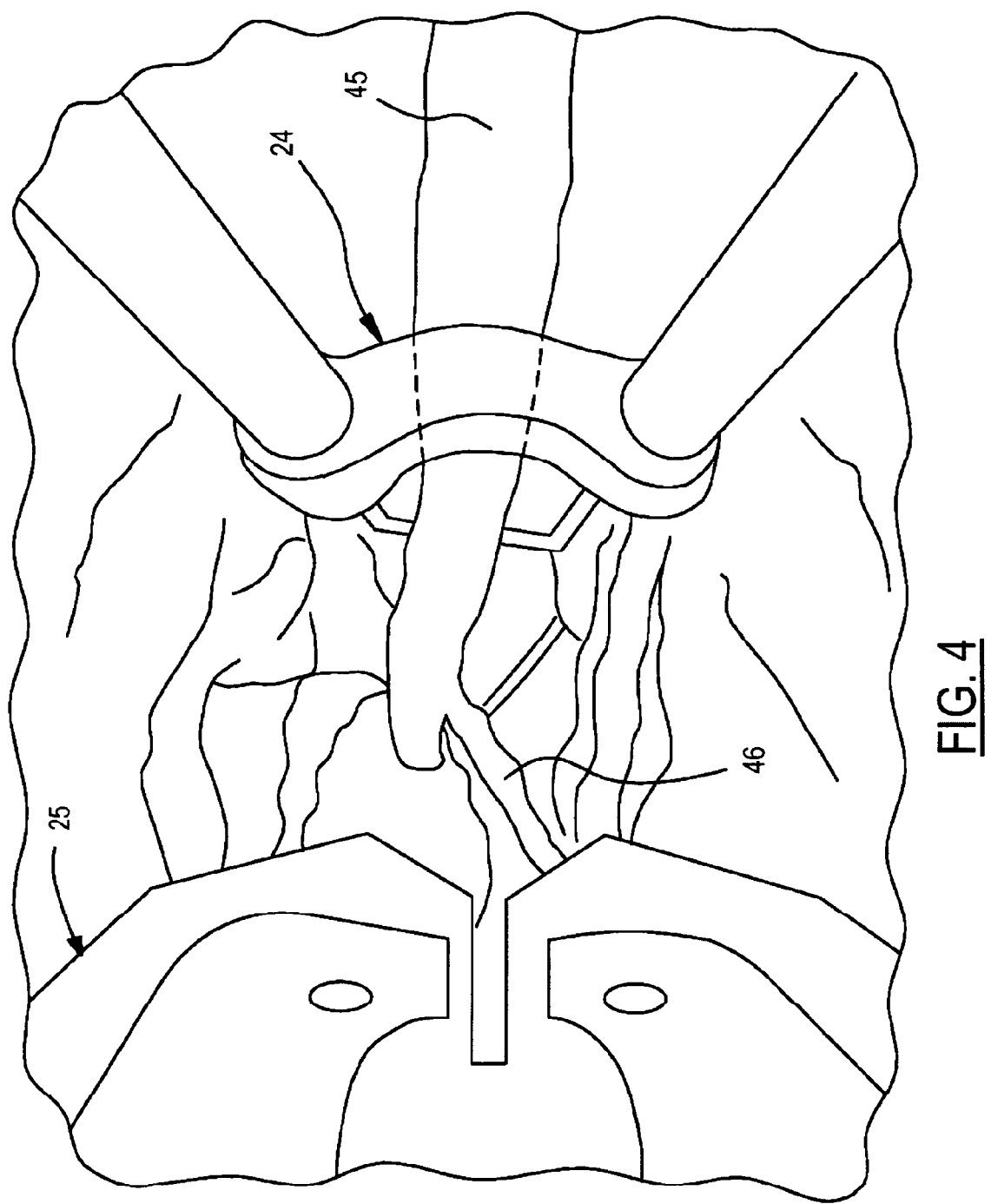
FIG. 4 is an endoscopic view of the harvester rod inside the body of a patient during harvesting of a vein.

Referring to FIG. 4, an endoscopic view is seen during vein harvesting wherein a vein being harvested 45 is retained within V-keeper 24 within the cavity around vein 45 created previously during blunt dissection. V-cutter 25 is in position for extending toward branch 46 for severing and cauterizing it to prepare vein 45 for removal.

Figure 5:
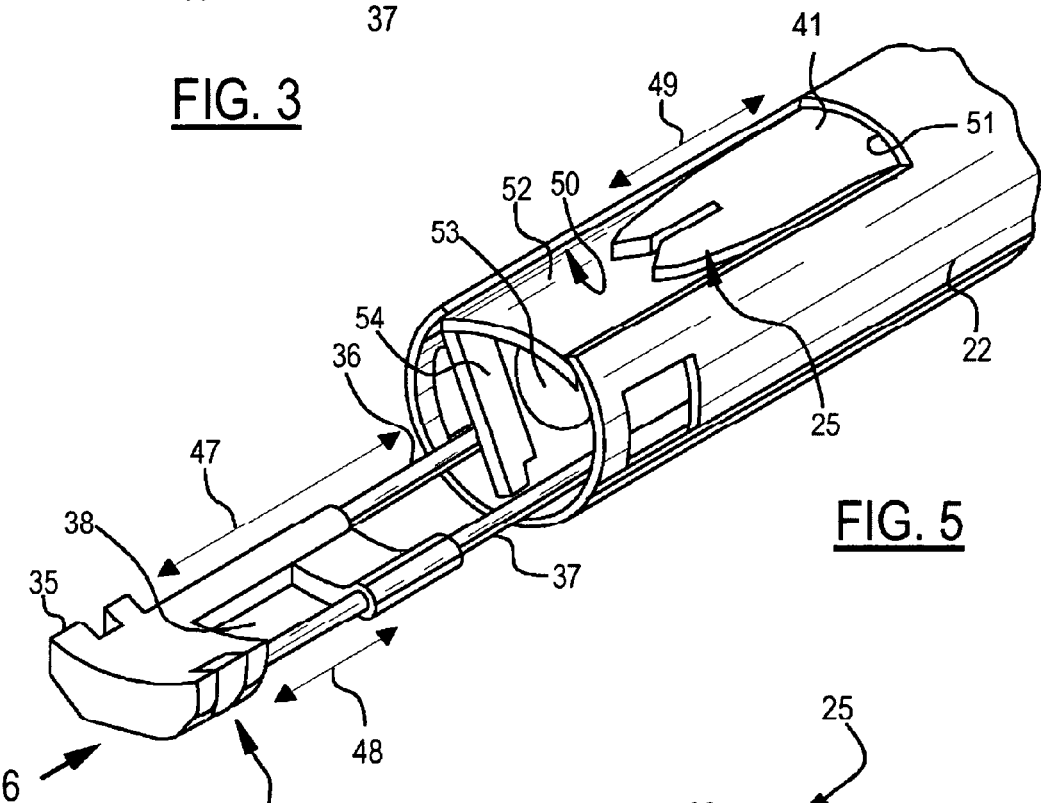
FIG. 5 is a perspective view of the distal end of the harvester rod showing extensibility of a V-keeper and a V-cutter.

FIG. 5 shows the distal end of harvester rod 20 in greater detail. V-keeper 24 is longitudinally extendable as shown by arrow 47 while pin 37 is independently longitudinally extendable as shown by arrow 48. As shown in FIG. 5, pin 37 has been extended to the position used for maintaining the vein being harvested within opening 38.

V-cutter 25 is longitudinally extendable in the directions shown by arrow 49. Elongated sleeve 22 has a notch 50 with a terminal edge 51 which exposes V-cutter 25 prior to being extended further than the end of sleeve 22. A guard piece 52 is provided beneath V-cutter 25. A lens portion 53 at the end of the endoscope is shown positioned near the distal end of sleeve 22. A wiper 54 is mounted for pivoting over lens 53 as controlled by lever 28 (FIG. 2) to wipe away debris from lens 53.

Figure 6:
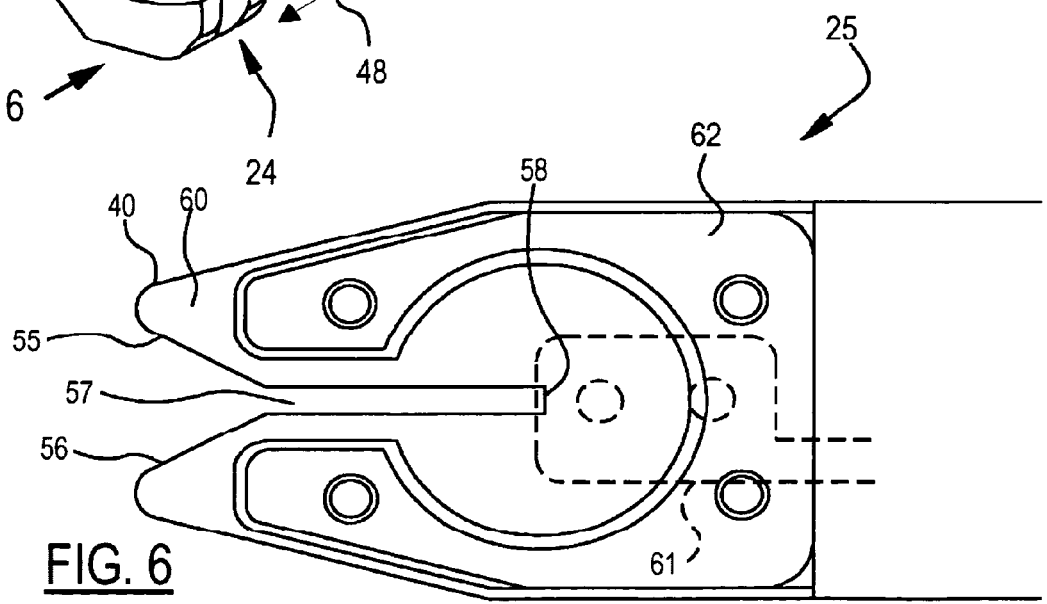
FIG. 6 is a top view of the V-cutter.

FIG. 6 shows V-cutter 25 in greater detail. V-tip 40 has angled surfaces 55 and 56 for guiding a vein into a longitudinal slit 57 having a terminus 58. An insulating base member 60 carries an applying electrode 61 on one side and a feedback electrode 62 on the opposite side. When a vessel to be severed is passing perpendicularly through longitudinal slit 57, a high frequency alternating voltage across electrodes 61 and 62 (from a generator, not shown) generates localized heating which severs and cauterizes the vessel.

After cutting and cauterizing many branches and/or connective tissue during the procedure to harvest a vessel, slit 57 may become clogged by debris such as fat, carbon, and remnants of burned tissue. Longitudinal slit 57 may have a width of about 1.0 mm for accommodating the size of all side branches to a saphenous vein, for example. When this narrow space becomes clogged, cutting and cauterizing efficiency is greatly reduced because the branches are unable to penetrate into the slit far enough to enter the area of maximum localized heating. Consequently, it has been necessary in the past to remove the harvesting rod in order to clean the V-cutter area by wiping with a gauze pad or gently sliding a length of suture material through the slit, for example. However, the increased duration of the procedure and the requirement to release the vessel from the V-keeper and again recapture it increase the risk of complications and/or damage to the vessel to be harvested.

The present invention solves the foregoing problems by providing a debris remover fixed to sleeve 22 for mechanically removing debris from the longitudinal slit when the cutter is positioned longitudinally inward from its cutting position. The debris remover is operable during times that the sleeve member is still inserted into the body, thereby avoiding the need to remove the harvester rod in order to clear debris from the slit. As shown in FIG. 7, one preferred embodiment of the invention utilizes a wiper arm 65 suspended from sleeve member 22 in longitudinal alignment with slit 57 and biased to impinge into and traverse along slit 57 as the V-cutter moves into and out of its inward position within notch 50. FIG. 7 shows V-cutter 25 extended out from its cleaning position wherein a tip 66 of wiper arm 65 rides along the upper surface of extendable guide 41. As shown in FIG. 8, when V-cutter 25 is moved to an inward position, wiper arm 65 springs down into slit 57 for mechanically removing or wiping away debris 64 so that it no longer clogs slit 57.

FIG. 9 is an end view showing wiper arm 65 extending into slit 57. Wiper arm 65 is mounted to an inner surface of longitudinal sleeve member 22 by an attachment 67 which may be comprised of an adhesive, for example. Also shown in FIG. 9 is a tip 68 of an insufflation tube for introducing $CO_2$ during vessel harvesting.

Wiper arm 65 may preferably include a plow-shaped profile as shown in FIGS. 10-12. Thus, wiper arm 65 includes an attachment base member 70 integral with an extension arm 71 having a tip 72. Extension arm 71 and tip 72 have a generally triangular cross section for slicing through and diverting or deflecting debris as the wiper arm moves through the slit.

FIGS. 13 and 14 illustrate the process for clearing debris from the longitudinal slit. As shown in FIG. 13, tip 66 of wiper arm 65 presses against the upper surface of extendable guide 41 when extendable guide 41 is extended toward its cutting position. As shown in FIG. 14, when extendable guide 41 and V-cutter 25 are withdrawn toward the inward-most position in the direction of arrow 73, tip 66 enters the slit and traverses along the slit to mechanically remove debris.

An alternative embodiment is shown in FIG. 15 wherein a nozzle 75 is mounted to sleeve member 22 at notch edge 51. Nozzle 75 is in longitudinal alignment with slit 57 for dispensing a fluid to clean the slit when it is moved to the inward position. FIG. 16 shows an end view wherein nozzle 75 is located directly above slit 57. Preferably, nozzle 75 may be oriented to direct discharged fluid slightly downward in the figure.

FIG. 17 shows V-cutter 25 retracted to its inward position facilitating the flow of fluid in a jet 76 from nozzle 75. The fluid may be comprised of a saline solution or a gas use for insufflation such as $CO_2$. Fluid is delivered to nozzle 75 by a fluid conduit 77 mounted within sleeve 22 and connected to a source of pressurized fluid 78. For example, source of pressurized fluid 78 may include a pump outputting a flow of saline solution to generate a spray from nozzle 75. The pump is operator controlled to coordinate creation of the spray with proper positioning of the V-cutter.

During an endoscopic procedure to harvest a vessel, the endoscopic vessel harvester is inserted into the body alongside the vessel to be harvested. The cutter is extended and the electrodes are energized (e.g., by a foot pedal operated by a surgeon) to individually sever a plurality of branches, wherein repeated cutting operations result in a build up of debris in the longitudinal slit. The cutter is then retracted to a position longitudinally inward from its cutting position while maintaining the endoscopic vessel harvester in the body so that the debris remover fixed to the sleeve member mechanically removes the debris from the longitudinal slit. After clearing the debris, the cutter may be extended to resume severing the branches. Patient outcome is improved since the vessel harvester need not be removed in order to clear the debris.

What is claimed is:

1. An endoscopic vessel harvesting device comprising:
    an elongated sleeve member for insertion into a body having a vessel to be harvested;
    a cutter longitudinally extendable from the sleeve member toward a cutting position for cutting branches of a vessel being harvested, the cutter comprising a V-tip and a longitudinal slit for receiving a branch to be cut, the cutter further comprising electrodes adjacent to the longitudinal slit for being electrically energized to cut and cauterize the branch; and
    a debris remover fixed to the sleeve member in alignment with the longitudinal slit for mechanically removing debris from the longitudinal slit when the cutter is positioned longitudinally inward from the cutting position, the debris remover being operable during times that the sleeve member is inserted into the body, wherein the debris remover comprises a wiper arm suspended from the sleeve member and biased to impinge into and traverse along the longitudinal slit as the cutter moves into and out of the inward position.

2. The device of claim 1 wherein the wiper arm is contoured to deflect debris away from the longitudinal slit.

3. The device of claim 2 wherein the wiper arm includes an attachment base integral with an extension arm, wherein the extension arm has a tip, and wherein the extension arm and tip have a generally triangular cross section.

4. A method of severing branches from a vessel during harvesting from a body by an endoscopic vessel harvester having an elongated sleeve member and a cutter, wherein the cutter is longitudinally extendable from the sleeve member toward a cutting position for cutting the branches, wherein the cutter comprises a V-tip and a longitudinal slit for receiving the branch to be cut, and wherein the cutter further comprises electrodes adjacent to the longitudinal slit for being electrically energized to cut and cauterize the branch, the method comprising the steps of:
    inserting the endoscopic vessel harvester into the body alongside the vessel to be harvested;
    extending the cutter and energizing the electrodes to individually sever a plurality of branches, resulting in a buildup of debris in the longitudinal slit;
    retracting the cutter to a position longitudinally inward from the cutting position while maintaining the endoscopic vessel harvester in the body so that a debris remover fixed to the sleeve member mechanically removes the debris from the longitudinal slit, wherein the debris remover comprises a wiper arm suspended from the sleeve member and biased to impinge into and traverse along the longitudinal slit as the cutter moves into and out of the inward position; and
    extending the cutter to resume severing the branches.

5. The method of claim 4 wherein the wiper arm is contoured to deflect debris away from the longitudinal slit.

6. The method of claim 5 wherein the wiper arm includes an attachment base integral with an extension arm, wherein the extension arm has a tip, and wherein the extension arm and tip have a generally triangular cross section.

\* \* \* \* \*